United States Patent
Bagnasco et al.

(10) Patent No.: US 8,388,625 B2
(45) Date of Patent: Mar. 5, 2013

(54) SUPPORT ORTHOPAEDIC DEVICE FOR A KNEE JOINT

(75) Inventors: Mara Bagnasco, Milan (IT); Daniele Venturini, Povegliano Veronese VR (IT); Graziano Marini, Castel d'Azzano VR (IT)

(73) Assignee: Orthofix S.R.L., Bussolengo VR (IT)

( * ) Notice: Subject to any disclaimer, the term of this patent is extended or adjusted under 35 U.S.C. 154(b) by 365 days.

(21) Appl. No.: 12/744,650

(22) PCT Filed: Sep. 10, 2009

(86) PCT No.: PCT/IB2009/006795
§ 371 (c)(1),
(2), (4) Date: May 25, 2010

(87) PCT Pub. No.: WO2010/029412
PCT Pub. Date: Mar. 18, 2010

(65) Prior Publication Data
US 2011/0034963 A1 Feb. 10, 2011

(30) Foreign Application Priority Data

Sep. 11, 2008 (IT) .............................. BO2008A0549

(51) Int. Cl.
*A61B 17/56* (2006.01)
(52) U.S. Cl. ................ 606/90; 606/57; 606/88
(58) Field of Classification Search ............. 16/221; 623/39–40; 606/54–59, 86 R, 87–88, 90; 269/3, 6, 95, 166, 246
See application file for complete search history.

(56) References Cited

U.S. PATENT DOCUMENTS

| | | | | |
|---|---|---|---|---|
| 3,985,127 A | * | 10/1976 | Volkov et al. ................. | 606/90 |
| 6,235,029 B1 | * | 5/2001 | Faccioli et al. ................ | 606/54 |
| 6,749,640 B1 | * | 6/2004 | Luhrs et al. .................... | 623/39 |

FOREIGN PATENT DOCUMENTS

| | | |
|---|---|---|
| DE | 19641131 | 4/1998 |
| GB | 2260083 | 4/1993 |
| GB | 2324038 | 10/1998 |
| WO | 88/03395 | 5/1988 |
| WO | 96/19944 | 7/1996 |

* cited by examiner

*Primary Examiner* — Todd Manahan
*Assistant Examiner* — Jessica Weiss
(74) *Attorney, Agent, or Firm* — Novak Druce Connolly Bove + Quigg LLP

(57) ABSTRACT

Support orthopaedic device (1) for a knee joint, comprising a proximal connector (2) and a distal connector (3), articulated among themselves and respectively intended to be associated with a proximal bone (100) and a distal bone (101) of a lower limb connected among themselves by a knee joint. The device comprises a first rod (4a) and a second rod (4b), which are hinged, according to hinging axes normal to a median excursion plane of the orthopaedic device (1), to the proximal connector (2) and to the distal connector (3) so as to form with them an articulated quadrilateral. The articulated quadrilateral is planarly mobile according to a plane parallel to the excursion plane between a configuration corresponding to an extended position of the knee joint and configurations corresponding to bendings of different entity of the knee joint; the relative motion imposed to the proximal and distal connectors (2, 3) by the articulated quadrilateral is consistent with the physiological movement of the knee joint.

12 Claims, 7 Drawing Sheets

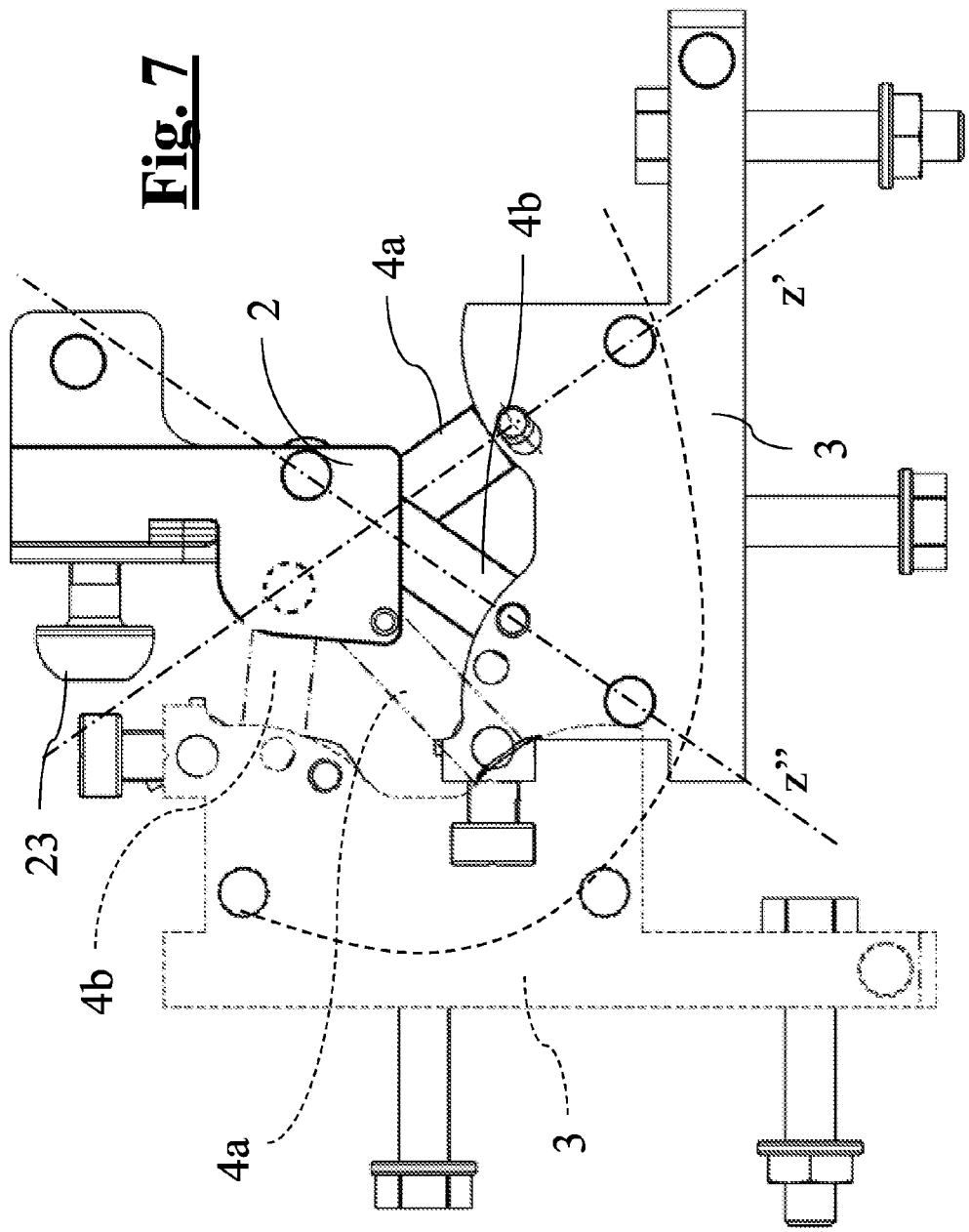

SUPPORT ORTHOPAEDIC DEVICE FOR A KNEE JOINT

CROSS-REFERENCE TO RELATED APPLICATIONS

This application is a §371 national stage entry of International Application No. PCT/IB2009/006795, filed Sep. 10, 2009, which claims priority to Italian Application No. BO2008A000549, filed Sep. 11, 2008, both of which are hereby incorporated herein by reference in their entirety.

FIELD OF APPLICATION

The present invention relates to a support orthopaedic device for a knee joint.

In particular, the device is of the type comprising a proximal connector and a distal connector, articulated to each other and intended to be respectively associated to a femoral bone and to a tibial bone of the lower limb of a patient, these bones being connected to each other through a knee joint.

PRIOR ART

Knee joint compartments may be subject to surgical operations for trauma or corrective treatment. Such operations, as in the general case of any orthopaedic operation, are characterized by a post-operational period in which the ossification process takes place; in this phase, it is generally necessary to ensure that the joint is not subjected to excessive loads.

The unloading of the joint may be obtained by total immobilization of the knee; on the other hand, this solution has substantial therapeutic drawbacks, and is therefore not often used.

A known alternative solution foresees the use of an orthopaedic device of the type mentioned above, which is provided for allowing partial or total transmission of loads through the operated joint.

In these cases, the proximal and distal connectors are generally associated to anchoring devices, which are respectively associated to the femoral and tibial bones of the patient.

A primary drawback of known orthopaedic devices is the articulation between the two connectors. In fact the relative movement imparted to the two connectors has to be unitary and above all has to reproduce in the most faithful manner possible the movements of the anchoring bones, which are physiologically determined by the natural joint. Such functional conditions are not ensured by simple and efficient constructive morphology. In fact, the coupling provided by the knee joint foresees a combination of rotations and relative slipping among the two affected bones, whose kinematics are difficult to reproduce with a reliable and small-sized mechanism. In fact, such a coupling cannot be reproduced by a simple hinge having a fixed rotational axis. In any case, a system is provided which allows the distraction of the joint, by moving the articulation contact surfaces farther away from each other in order to allow a minimal rotational movement, even if the device does not faithfully reproduce traditional joint movement.

A second problem arising from the therapeutic use of orthopaedic devices according to the known art is the precise positioning of the same device with respect to the bone structure of the patient. In particular, it is of fundamental importance that the articulation of the two connectors is provided on a plane that is normal to the articulation axis of the lower limb. The known anchoring devices are associated, by means of screws, to suitable bone sites on the femur and tibia. The bone surface in these sites is not normal with respect to the articulation axis; as a result there is no morphological reference that may guide the fixing operation of the orthopaedic device. Moreover, the attachment sites are relatively remote from the joint compartment, further complicating the problem regarding a proper positioning of the orthopaedic device.

The technical problem which the present invention has to solve is therefore to provide an orthopaedic device having a structure that overcomes said drawbacks of the known art.

SUMMARY OF THE INVENTION

This technical problem is solved by an orthopaedic device of above said type, also comprising a first rod and second rod that are hinged to each other along hinging axes that are normal to a median excursion plane of the orthopaedic device 1 itself, to the proximal connector and to the distal connector, so as to form with them a four-bar linkage. The four-bar linkage is planarly mobile along a plane parallel to the excursion plane, between a main configuration corresponding to an extended position of the knee joint and a plurality of secondary configurations corresponding to different degrees of bending of the knee joint; in particular, the relative motion imposed on the proximal and distal connectors by the four-bar linkage is consistent with the physiological movement of the knee joint.

In general, the idea of the present invention is to reproduce the flexing and extending movements of the knee joint by means of a four-bar linkage, two opposed members of which are provided by the connectors. This constructive solution allows for a reduced size and complexity of the orthopaedic device, while on the other hand ensuring the relative movement of the different elements to reproduce, in a sufficiently faithful manner, the physiological movement of the knee joint.

An advantage of the invention is the fact that the device according to the present invention is easily positioned and modularly assembled with other known orthopaedic devices, ensuring a fast and precise implant.

Further characteristics and advantages will be more clearly understood from the following detailed description of a preferred embodiment of the present invention, which is non-limiting, with reference to the attached figures, which are illustrative but not limiting in scope.

BRIEF DESCRIPTION OF THE DRAWINGS

FIG. 7 shows a diagram reproducing the kinematics of the four-bar linkage facilitating articulation of the device of FIG. 1.

DETAILED DESCRIPTION

Figure 1:
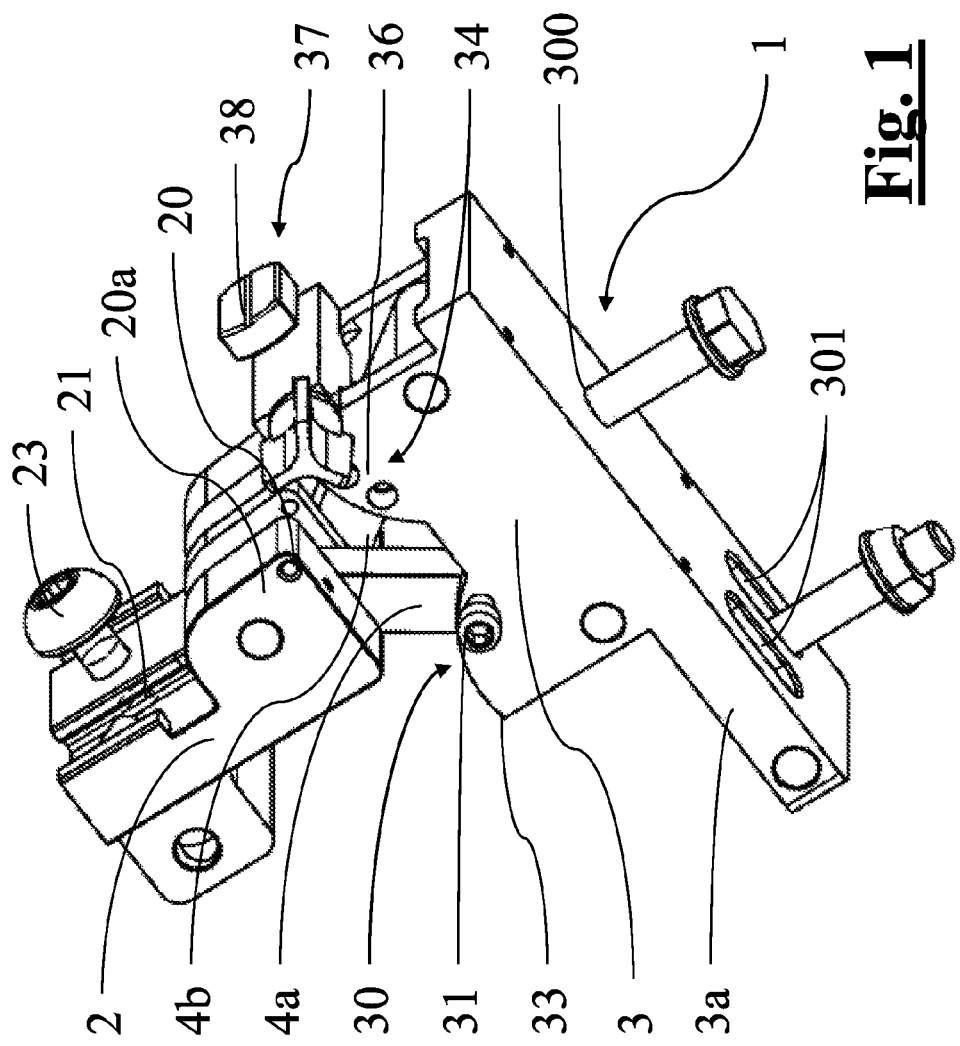
FIG. 1 shows an isometric view of an orthopaedic device according to the invention.
Figure 2:
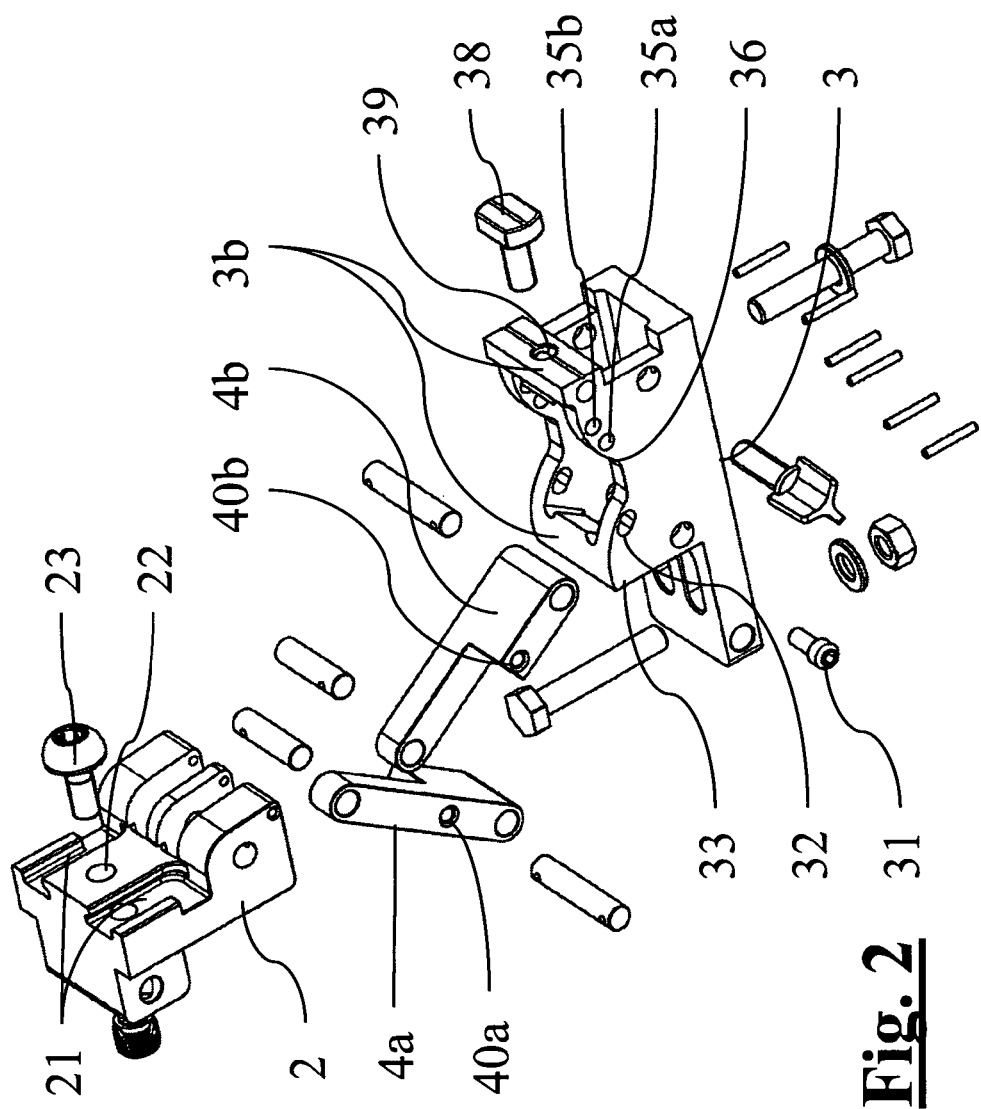
FIG. 2 shows an exploded view of various components of the orthopaedic device of FIG. 1.
Figure 3:
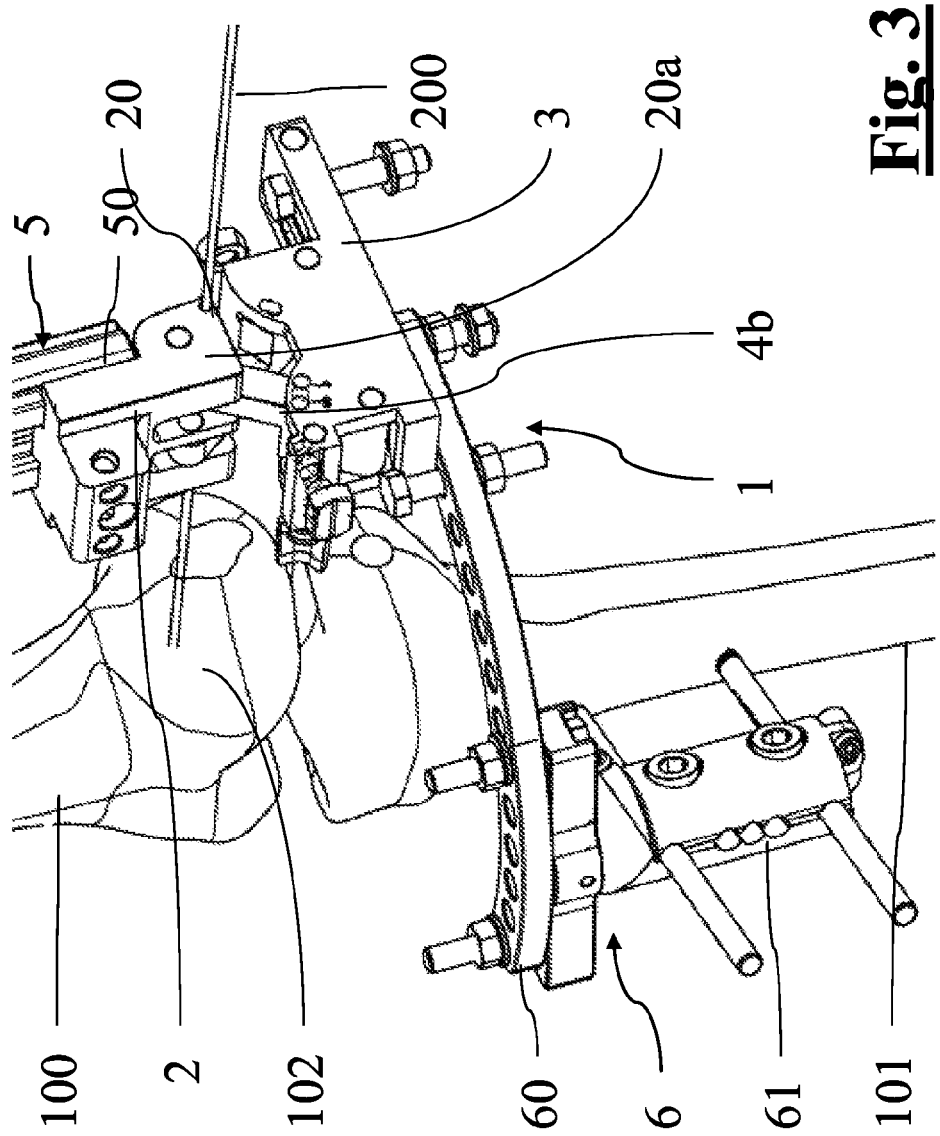
FIG. 3 shows an isometric view of the orthopaedic device of FIG. 1, associated to a knee joint, which is extended by means of known anchoring devices.

With reference to the appended figures, reference numeral 1 indicates a support orthopaedic device for a knee joint. The primary task of such a device, as already said, is to transmit the same loads that would otherwise act on the joint, allowing for proper healing during the post-surgery period and at the same time ensuring an at least partial mobility of the affected lower limb.

The orthopaedic device 1 comprises a proximal connector 2 and a distal connector 3, which are articulated to each other and are provided to be respectively associated to a proximal bone 100 and distal bone 101 of a lower limb, which are connected to each other by means of the knee joint. In particular, in the preferred embodiment of the appended figures the proximal bone 100 is the femur of the patient, whereas the distal bone 101 is advantageously the tibia.

Said orthopaedic device 1 also comprises a first rod 4a and a second rod 4b, said rods 4a, 4b being hinged, along hinging axes that are normal to a median excursion plane of the same device, to proximal connector 2 and distal connector 3, in order to form a four-bar linkage with them.

The four-bar linkage, which is schematically shown in FIG. 7, is therefore comprised of a frame operatively provided by proximal connector 2, two balance beams which are provided by rods 4a and 4b and by a push rod, which is provided by distal connector 3.

The four-bar linkage is planarly mobile according to a plane which is normal to the excursion plane between a main configuration corresponding to an extended position of the knee joint and a plurality of secondary configurations corresponding to different degrees of bending of the knee joint; the relative motion imparted to the proximal and distal connector 2, 3 by the four-bar linkage is consistent with the physiological movement of the knee joint.

As can be seen in attached FIGS. 3-6, the proximal connector 2 of orthopaedic device 1 is provided for direct connection to a first anchoring device 5, which is provided for being fixedly associated to the proximal bone 100, i.e. the femur; whereas the distal connector 3 is provided for direct connection to a second anchoring device 6, provided for being fixedly associated to the distal bone 101, i.e. the tibia.

The first anchoring device 5, in the preferred embodiment, comprises a longitudinal rail 50, provided with at least a first clamp 51 which may be associated to a femoral surface by means of an assembly of bone screws. The bone screws are advantageously inserted into a femur, which, as previously said, extends along a longitudinal axis x that is not perpendicular to the joint axis y of the limb (in particular, the angle between the two is approximately) 81°. The first clamps 51 may be adjusted with respect to the longitudinal rail 50. The attachment site of the bone screws is preferably located on a lateral surface of the femur; therefore device 1, which is rigidly fixed to the distal end of the longitudinal rail 50, is in a lateral position with respect to the lower limb.

In an alternative embodiment of present invention, not shown, the first anchoring device 5 may comprise a ring, or a ring portion, which is connected to proximal connector 2.

Figure 6:
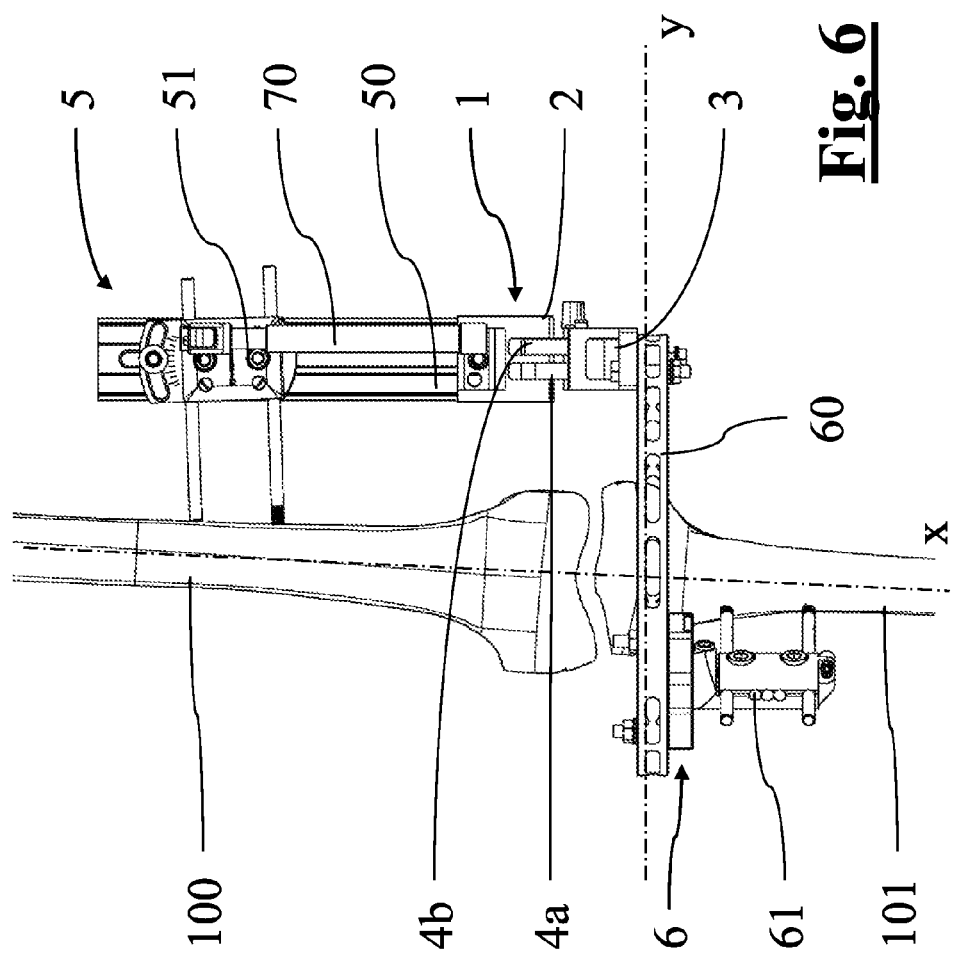
FIG. 6 shows a front view of a tibia-femur group, to which the orthopaedic device of FIG. 1 is associated by means of known anchoring devices.

As can readily be seen in FIG. 6, a compressor 70 may be associated to first anchoring device 5, in order to distract both distal 3 and proximal connectors 2, in order to create a space in the joint. Once the joint has been distracted, indicatively by 2-10 mm, the compressor may be removed.

The second anchoring device 6 comprises a rigid half ring 60 and a second clamp 61 that can be associated to a tibial surface by means of bone screws. Thanks to the provision of the rigid half ring it is possible to associate the bone screws of the second clamp 61 to the front surface or middle-front surface of the tibia, taking advantage of the most suitable sites for such an implant.

As discussed before, for a proper operation of the orthopaedic device the excursion plane of the device has to be normal to the articulation axis of the lower limb, identified by x in FIG. 6. In order to ensure these conditions of the orthopaedic device 1, it comprises means for precise positioning of at least one of the proximal or distal connector 2, 3 with respect to the corresponding bone, i.e. the femur for proximal connector 2 or the tibia for distal connector 3.

In particular, said means for precise positioning comprise a first portion 20a of one of the connectors 2, 3, said portion 20a having at least a reference hole 20 to temporarily receive a guide thread 200 which is fixed to the bone of the corresponding connector; advantageously, the reference hole 20 is normal to the excursion plane.

Figure 4:
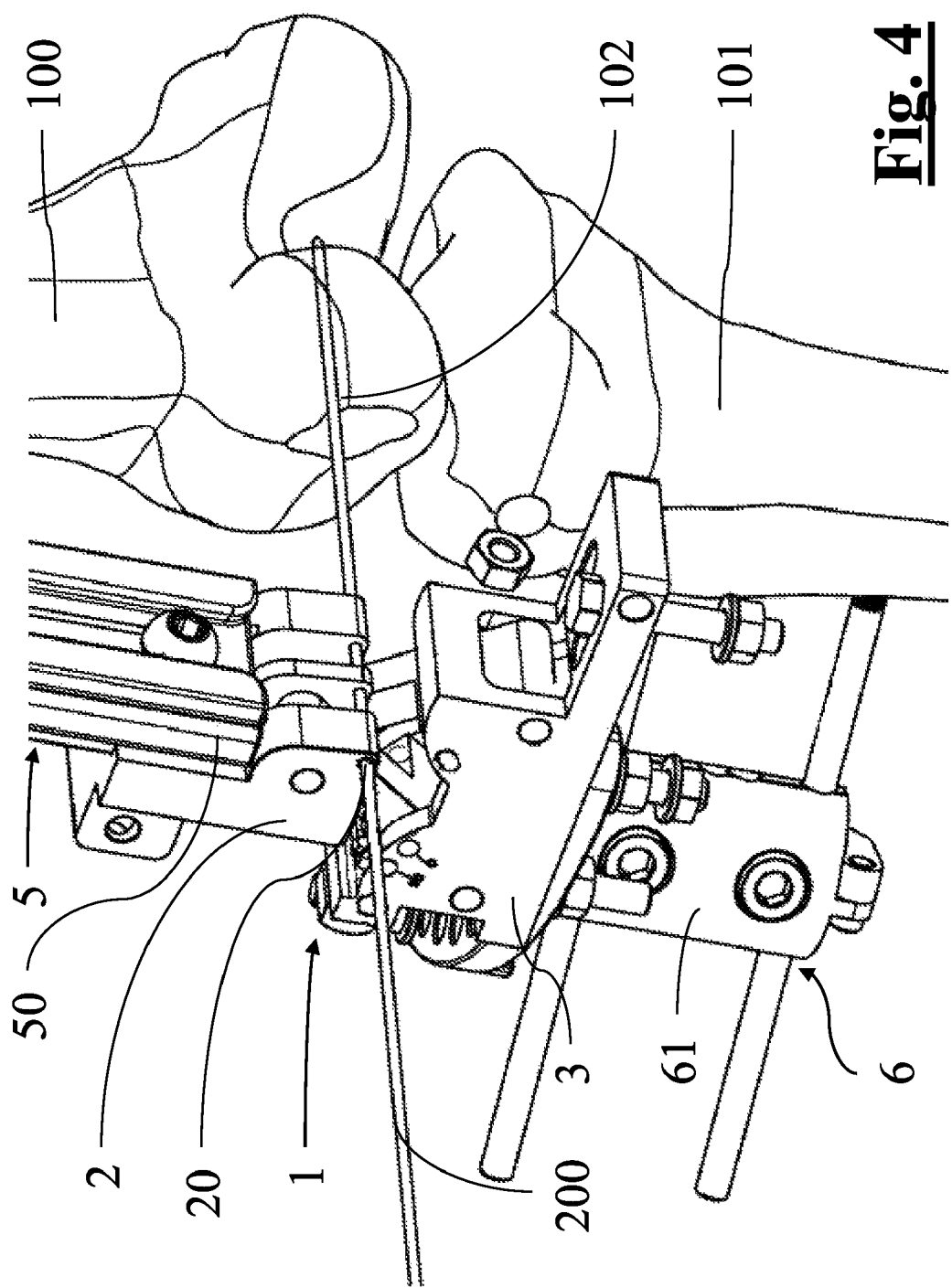
FIG. 4 shows an isometric view of elements represented in FIG. 3, from a different perspective.
Figure 5:
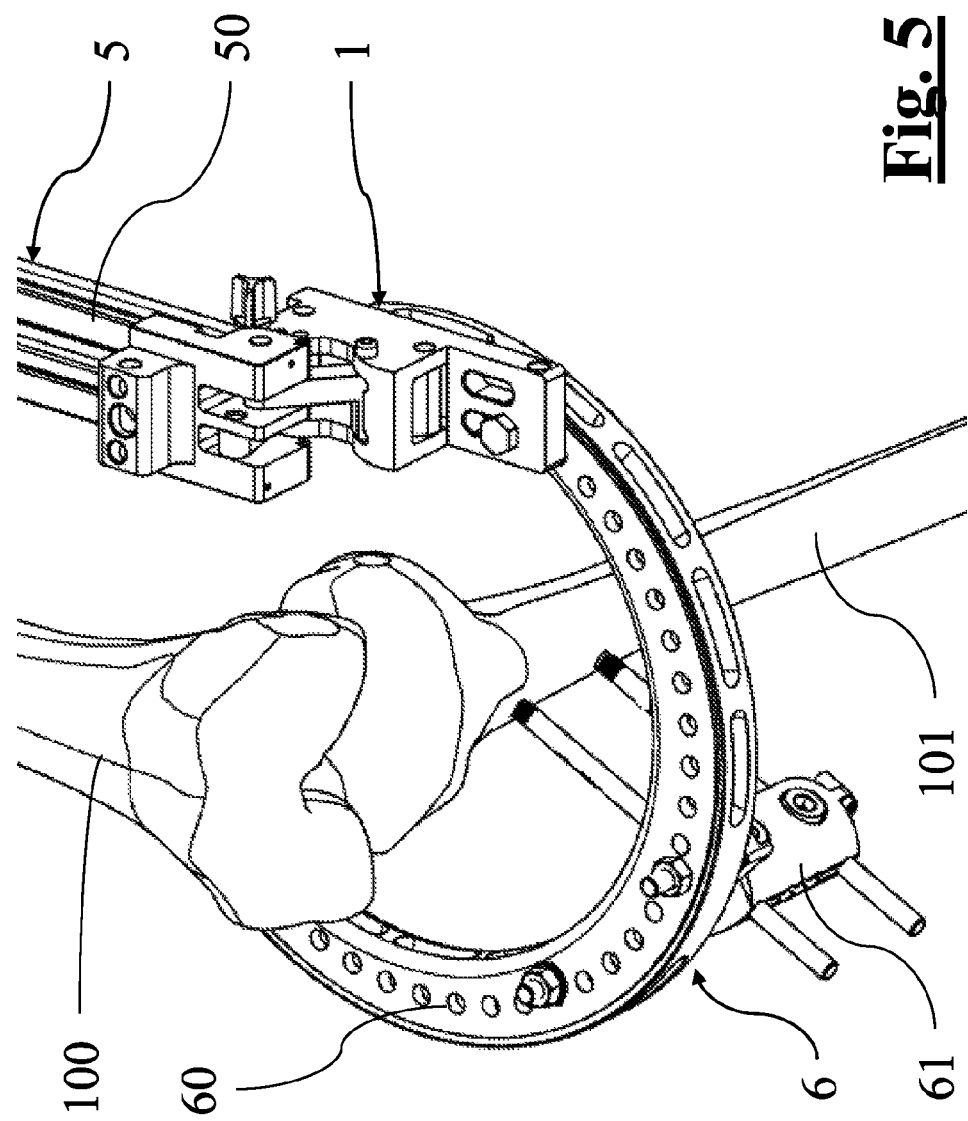
FIG. 5 shows an isometric view of elements represented in FIG. 3, with a flexed knee joint.

In the preferred embodiment shown, the first portion 20a is provided on the proximal connector 2, and the reference hole 20 is positioned on a distal end of connector 2, with respect to the proximal bone 100 to which it is associated. In this way, as shown in FIG. 4, the guide thread 200 is suitably introduced into a cannula screw that is inserted in the medial epicondyle 102 of the patient. By means of morphological references near the epicondyle the cannula screw can be readily positioned so that it is parallel to the articulation axis y of the knee. The guide thread 200 is also parallel to the articulation axis y and its insertion into the reference hole 20 causes the excursion plane of orthopaedic device 1 to be orthogonal to this axis. The guide thread 200 has no structural purpose and is removed once the orthopaedic device 1 has been implanted.

From an operational point of view, a method for fixing the device according to the invention to the bone structure of a patient comprises the following steps: an insertion step of a thread in the femoral channels in a direction parallel to the articulation axis y of the limb, followed by anchoring of the proximal connector 2 and the distal connector 3 to the bone structure of patient, by means of said anchoring means 5, 6.

The diagram of FIG. 7 shows the positions of the members forming the four-bar linkage in the case of the main configuration and of a secondary configuration corresponding to bending at a substantially right angle of the knee joint. In the diagram the trajectory of a point of the distal connector 3 corresponding to a change of the bending angle of the tibia, with a fixed position of the proximal connector, is also shown. Such a trajectory, which is substantially the same as the trajectory provided by the articular movement of a healthy knee, is obtained by the following constructive means.

First of all, the four-bar linkage used is a Grashof mechanism, in which the relative excursion of links is however operatively limited at least by the anchoring to the bone structures of the lower limb.

The first and second rod 4a, 4b which comprise the four-bar linkage, cross each other at least in their main configuration. In particular, the four-bar linkage remains inverted for the better part of its operative configurations, wherein by operative configurations one refers to the main configuration and secondary configurations which are operatively feasible. The inverted position of the four-bar linkage allows the instant centre of rotation of the device to be held inside the four-bar linkage's volume, thereby constraining the instant axis of rotation near the knee joint. In fact, as per Chasles' theorem, the instant centre of rotation is at the crossing C of the longitudinal axes z', z'', shown in FIG. 7, of the two rods 4a, 4b, which form the balance rods of the four-bar linkage.

In particular it would be advantageous if an inversion configuration, i.e. a dead point configuration, were to form part of the group of secondary configurations; in this case such a configuration corresponds to a bending at a substantially right angle of the knee joint.

Advantageous dimensional characteristics of the four-bar linkage according to the invention comprise: a ratio of the distance between hinging axes and the first and second rods 4a, 4b of distal connector 3 and the distance between hinging axes and the first and second rods 4a, 4b of the proximal connector 2 higher than 1, and preferably comprised between 3.5 and 4.3 (the value of the ratio in the illustrated embodiment is 43/11); a ratio of the distances of the opposed hinging axes in relation to first and second rods 4a, 4b between 0.9 and 1.1 and preferably equal to 1, as in the illustrated embodiment; ratio of distances of the opposed hinging axes of first rod 4a and the distance between the hinging axes of first and second rods 4a, 4b of distal connector 3 higher than 1 and preferably lower than 1.2 (the value of the ratio in the illustrated embodiment is 47/43). Obviously, all these values are absolutely non-limiting with reference to the present invention.

The orthopaedic device 1 according to the invention advantageously comprises: first locking means 30 provided for locking the four-bar linkage in the main configuration or in any one of its secondary configurations; second locking means 34 provided for locking the four-bar linkage in a finite plurality of possible locking configurations; stop means 37 adjustable for unilaterally limiting the excursion of the four-bar linkage in order to inhibit the bending of the knee joint to which the device 1 is associated.

At least one of first and second rod 4a, 4b comprises a first transversal threaded hole 40a, with axis normal to the excursion plane of device 1; the first locking means 30 comprise a locking screw 31, insertable into the first transversal hole 40a and into a slot 32 of a first septum 33, integral with one of the distal or proximal connectors 2, 3. Therefore the locking screw 31 may be clamped against the wall of the first septum 33 peripheral to slot 32, allowing the four-bar linkage to be locked in a desired configuration.

At least one of the first and second rods 4a, 4b features a second transversal hole 40b with axis normal to the excursion plane of the device 1. The second locking means 34 comprise a second septum 36 integral with one of the distal or proximal connectors 2, 3, which features a plurality of locking holes 35a, 35b (although, as said, the real locking of the device is preferably obtained by means of locking screw 31 of first locking means 30, and these holes are mainly used as references for the degree of articulation bending). Each of the locking holes 35a, 35b is aligned with the second transversal hole 40b at a possible locking configuration. In these configurations, it suffices to insert a pin through the two holes to lock the rod to the connector, therefore locking the four-bar linkage in the desired locking configuration.

In the preferred embodiment shown, the two locking holes 35a, 35b allow the four-bar linkage to be locked in above said main configuration, and in a secondary configuration corresponding to a right angle bend of the limb associated with device 1.

The stop means 37 comprise a stop screw 38, insertable into a threaded stop hole 39. The stop hole 39 is integral with one of the connectors 2, 3 and has an axis which is parallel to the excursion plane of device 1. The end of the stop screw 38 is provided in order to interfere with the movement of at least one of the rods 4a, 4b through contact, limiting the excursion of the four-bar linkage. In this case, it is provided for interfering with the rotation of the second rod 4b.

A rotation of the locking screw 38 about its axis corresponds to its traversing along the axis of locking hole 39; in this way it is possible to modify the position of the end of the screw provided for limiting the angular excursion of rod 4a, 4b, by adjusting the maximum bending angle of the device.

Advantageously, the screw and the four-bar linkage are formed in order to provide a substantially linear relationship between the angle of rotation of the screw and variation of the maximum excursion angle of the limb associated to the device 1.

Structurally, the first septum 33, the second septum 36 and stop hole 39 are all integral with the distal connector 3. In particular, this distal connector comprises a base 3a, from which two lateral walls laterally rise, forming a hinging bracket for first rod 4a and second rod 4b. These lateral walls are parallel to the excursion plane of device 1 and are contiguous to both hinged rods 4a, 4b. The first septum 33 and second septum 36, as shown in the appended figures, are part of one of these walls.

The first transversal hole 40a is provided on the first rod 4a, whereas the second transversal hole 40b is provided on the second rod 4b. The rods are preferably identical, with a first segment hinged to distal connector 3, having a transversal extension equal to the distance between the lateral walls of the connector; a second segment, hinged to proximal connector 2, having a reduced transversal extension in order to allow the two members to cross without interference.

Slot 32 has a circular arc shape with centre on the hinging axis of first rod 4a to distal connector 3. The terminal portion of locking screw 31, when unclamped, slides within this circular arc; in any case, slot 32 limits the angular excursion of first rod 4a.

The two lateral walls of distal connector 3, which are inferiorly joined by base 3a, are joined on the upper side by cross beams 3b. Such cross beams are lateral with respect to the free central space inside of which the first and second rod 4a, 4b may move.

One of the beams 3b, in particular the one nearer to the second rod 4b, has a stop hole 39 for inserting the stop screw 38. This beam also has a hole with an axis that is normal to that of the stop hole 39, inside which a screw is inserted that interacts with the stop screw 38 in order to lock it in the desired position.

The base 3a of the distal connector 3 is provided for association with the above-mentioned rigid half ring 60, which is mounted in a distal position underneath the base 3a. To this end, the base 3a provides suitable connecting means, i.e. a central hole 300 on the bottom of the bracket defined by the lateral walls, as well as longitudinal slots 301 provided on a portion of the base which is not surmounted by lateral walls. These openings allow insertion of fixing screws of the rigid half ring 60, as shown in FIGS. 3-6.

The proximal connector 2 comprises, at its distal end (always referring to the femoral bone, to which it is associated) two side-by-side brackets, into which the second segments of first rod 4a and second rod 4b are inserted and hinged, according to parallel but offset axes. Reference hole 20, which is preferably a through hole, is provided on the distal end of both brackets, in a lateral position with respect to the central free space inside of which first and second rod 4a, 4b may move.

The proximal portion of the proximal connector 2 is advantageously arranged in such a way as to be associated to a longitudinal rail 50 of above said type. To this end, it comprises suitable connection means, i.e. two shaped and parallel grooves 21 and at least one main threaded seat 22 for inserting a locking member 23 of the longitudinal rail.

Obviously, in order to meet contingent and specific needs a person skilled in the art may introduce various modifications and variations to above said orthopaedic device, which are all within the scope of protection of the invention, as defined by the following claims.

The invention claimed is:

1. Support orthopaedic device for a knee joint, comprising
a first anchoring device and a second anchoring device, arranged to be integrally associated respectively with a proximal bone and a distal bone of a lower limb connected among themselves by a knee joint,
a proximal connector and a distal connector, articulated among themselves and respectively intended to be directly connected to said first and a second anchoring devices,
a first rod and a second rod hinged, according to hinging axes normal to a median excursion plane of the orthopaedic device, to the proximal connector and to the distal connector so as to form with them a four-bar linkage; said four-bar linkage being planarly mobile according to a plane parallel to the excursion plane between a main configuration corresponding to an extended position of the knee joint and a plurality of secondary configurations corresponding to a different degree of bending of the knee joint, the relative motion imposed to the proximal and distal connectors by the four-bar linkage being consistent with the physiological movement of the knee joint,
wherein said proximal connector presents, in correspondence with one of its distal ends, a reference hole, normal to the excursion plane, intended to temporarily house a guide thread integral with the proximal bone to allow the accurate positioning of the proximal connector with respect to the bone,
wherein the device comprises first means to lock arranged to allow the locking of the four-bar linkage in the main configuration or in any one of its secondary configurations, and
wherein at least one of the first and second rods has a first transversal threaded hole with axis normal to the excursion plane of the device; the first means to lock comprising a locking screw, insertable into the first transversal hole and into a slot of a first septum integral with one of the distal or proximal connectors; said locking screw being clampable against a wall of the first septum to lock the four-bar linkage in a wanted configuration.

2. Orthopaedic device 1 according to claim 1 wherein said proximal connector has means to connect arranged to hold a longitudinal rail of the first anchoring device.

3. Orthopaedic device according to claim 1 wherein said distal connector has means to connect arranged to fasten the connector to a rigid half ring of the second anchoring device.

4. Orthopaedic device according to claim 1 wherein the first rod and the second rod are crossed at least in the main configuration.

5. Orthopaedic device according to claim 4, wherein the ratio between the distance between the hinging axes of the first and the second rods to the distal connector and the distance between the hinging axes of the first and second rods to the proximal connector is comprised between 3.5 and 4.3.

6. Orthopaedic device according to claim 5, wherein the ratio between the distances of the hinging axes of the first rod and the distance of the hinging axes of second rods is comprised between 0.9 and 1.1.

7. Orthopaedic device according to claim 6, wherein the ratio between the distance of the hinging axes of the first rod and the distance between the hinging axes of the first and second rods to the distal connector is comprised between 1 and 1.2.

8. Orthopaedic device according to claim 1, wherein the first transversal hole is arranged on the first rod, the first septum being integral with the distal connector, parallel to the excursion plane of the device and contiguous to the first rod, the slot having the shape of a circular arc with the centre on the hinging axis of the first rod to the distal connector.

9. Orthopaedic device according to claim 1, comprising means to stop positionable to unilaterally limit the excursion of the four-bar linkage so as to limit the bending of the knee joint to a wanted angle.

10. Orthopaedic device according to claim 9, wherein the means to stop comprise a stop screw, insertable into a threaded stop hole integral with one of the connectors and with axis parallel to the excursion plane of the device, one end of the stop screw being arranged to interfere by contact with at least one of the rods, by limiting the excursion of the four-bar linkage.

11. Support orthopaedic device (1) for a knee joint, comprising a proximal connector (2) and a distal connector (3), articulated among themselves and respectively intended to be directly connected to
a first anchoring device and to a second anchoring device (5, 6), arranged to be integrally associated respectively with a proximal bone (100) and a distal bone (101) of a lower limb connected among themselves by a knee joint,
a proximal connector and a distal connector, articulated among themselves and respectively intended to be directly connected to said first and a second anchoring devices; characterised in that it comprises
a first rod (4a) and a second rod (4b); said first and second rods (4a, 4b) being hinged, according to hinging axes normal to a median excursion plane of the orthopaedic device (1), to the proximal connector (2) and to the distal connector (3) so as to form with them an four-bar linkagearticulated quadrilateral; said four-bar linkagearticulated quadrilateral being planarly mobile according to a plane parallel to the excursion plane between a main configuration corresponding to an extended position of the knee joint and a plurality of secondary configurations corresponding to different degree of bendings of different entity of the knee joint, the relative motion imposed to the proximal and distal connectors (2, 3) by the four-bar linkagearticulated quadrilateral being consistent with the physiological movement of the knee joint,
wherein said proximal connector (2) presenting, in correspondence with one of its distal ends, a reference hole (20), normal to the excursion plane, intended to temporarily house a guide thread (200) integral with the proximal bone (100) to allow the accurate positioning of the proximal connector with respect to the bone,
wherein the device comprises a second means to lock arranged to allow the locking of the four-bar linkage in a finite plurality of possible locking configurations, and
wherein at least one of the first and second rods has a second transversal hole with axis normal to the excursion plane of the device; the second means to lock comprising a second septum integral with one of the distal or proximal connectors, said second septum comprises a plurality of locking holes, one of which is aligned with the second transversal hole at a possible locking configuration, a pin being therefore insertable through one of the locking holes and the second transversal hole to lock the four-bar linkage in the wanted locking configuration.

12. Support orthopaedic device for a knee joint, comprising a first anchoring device and a second anchoring device, arranged to be integrally associated respectively with a proximal bone and a distal bone of a lower limb connected among themselves by a knee joint, a proximal connector and a distal connector, articulated among themselves and respectively intended to be directly connected to said first and a second anchoring devices, a first rod and a second rod hinged, according to hinging axes normal to a median excursion plane of the orthopaedic device, to the proximal connector and to the distal connector so as to form with them a four-bar linkage; said four-bar linkage being planarly mobile according to a plane parallel to the excursion plane between a main configuration corresponding to an extended position of the knee joint and a plurality of secondary configurations corresponding to different degree of bending of the knee joint, the relative motion imposed to the proximal and distal connectors by the four-bar linkage being consistent with the physiological movement of the knee joint, wherein said proximal connector presents, in correspondence with one of its distal ends, a reference hole, normal to the excursion plane, intended to temporarily house a guide thread integral with the proximal bone to allow the accurate positioning of the proximal connector with respect to the bone; means to stop positionable to unilaterally limit the excursion of the four-bar linkage so as to limit the bendings of the knee joint to a wanted angle, wherein the means to stop comprise a stop screw, insertable into a threaded stop hole integral with one of the connectors and with axis parallel to the excursion plane of the device, one end of the stop screw being arranged to interfere by contact with at least one of the rods, by limiting the excursion of the four-bar linkage; wherein the distal connector comprises two side walls which rise laterally in relation to a base to form a hinging bracket for the first rod and the second rod, said rods both having a first segment, hinged to the distal connector, with transversal extension equal to the distance between the side walls and a second segment, hinged to the proximal connector, with reduced transversal extension compared to the first segment to allow crossing without interference of the two rods; the proximal connector comprising two side-by-side brackets, inside which, according to parallel but offset axis, the second segments of the first rod and the second rod are introduced and hinged.

* * * * *